(12) United States Patent
Wolf et al.

(10) Patent No.: US 6,730,635 B2
(45) Date of Patent: May 4, 2004

(54) MICROCAPSULE SUSPENSIONS

(75) Inventors: Hilmar Wolf, Langenfeld (DE); Norbert Schick, Solingen (DE); Björn Christensen, Leverkusen (DE); Anne Suty-Heinze, Langenfeld (DE)

(73) Assignee: Bayer AG, Leverkusen (DE)

( * ) Notice: Subject to any disclaimer, the term of this patent is extended or adjusted under 35 U.S.C. 154(b) by 0 days.

(21) Appl. No.: 10/221,464

(22) PCT Filed: Mar. 6, 2001

(86) PCT No.: PCT/EP01/02483

§ 371 (c)(1),
(2), (4) Date: Sep. 12, 2002

(87) PCT Pub. No.: WO01/68234

PCT Pub. Date: Sep. 20, 2001

(65) Prior Publication Data

US 2003/0119675 A1 Jun. 26, 2003

(30) Foreign Application Priority Data

Mar. 17, 2000 (DE) .......................... 100 13 127
Nov. 27, 2000 (DE) .......................... 100 58 878

(51) Int. Cl.⁷ .............................................. A01N 25/28
(52) U.S. Cl. ..................... 504/359; 514/341; 514/624; 514/963
(58) Field of Search ......................... 504/359; 514/341, 514/624, 963

(56) References Cited

U.S. PATENT DOCUMENTS

| 4,280,833 | A | * | 7/1981 | Beestman et al. | 71/100 |
| 4,610,927 | A | * | 9/1986 | Igarashi et al. | 428/402.21 |
| 5,433,953 | A | * | 7/1995 | Tsuei et al. | 424/489 |
| 5,846,554 | A | | 12/1998 | Scher et al. | 424/408 |
| 6,015,571 | A | | 1/2000 | Scher et al. | 424/408 |
| 6,077,522 | A | | 6/2000 | Scher et al. | 424/408 |
| 6,149,843 | A | | 11/2000 | Scher et al. | 264/4.1 |

FOREIGN PATENT DOCUMENTS

| DE | 198 40 582 | 3/2000 |
| DE | 198 40 583 | 3/2000 |

OTHER PUBLICATIONS

*Database WPI Section Ch, Week 198337 Derwent Publications Ltd., London, GB; AN 1983–762720 XP002172794 & RO 76 732 A (Inst Chim Macromoleculara Petru Poni), Feb. 28, 1983 Zusammenfassung.
*Database WPI Section Ch, Week 198337 Derwent Publications Ltd., London, GB; AN 1983–762721 XP002172795 & RO 76 733 A (Inst Chim Macromoleculara Petru Poni), Feb. 28, 1983 Zusammenfassung.

* cited by examiner

Primary Examiner—S. Mark Clardy
(74) Attorney, Agent, or Firm—Richard E. L. Henderson

(57) ABSTRACT

The invention relates to microcapsule suspensions containing (A) a particulate disperse phase of microcapsules comprising:
  (1) sleeves that are reaction products of mixtures of toluylene diisocyanate and 4,4'-methylenebis-(cyclohexyl isocyanate) with at least one diamine and/or polyamine, and
  (2) a capsule filling comprising:
    (i) at least one solid insecticidally and/or herbicidally active compound,
    (ii) at least one liquid aliphatic hydrocarbon having a boiling point above 160° C.,
    (iii) at least one oil-soluble polymeric dispersing agent, and
    (iv) optional agrochemically active compounds that are liquid at room temperature, and
(B) a liquid aqueous phase comprising water, optional additives, and optional agrochemically active compounds in non-encapsulated form that are solid at room temperature.

6 Claims, No Drawings

MICROCAPSULE SUSPENSIONS

The present invention relates to novel microcapsule suspensions, to a process for their preparation and to their use for applying agrochemically active compounds.

Microcapsule formulations which comprise, in the capsules, suspensions of solid agrochemically active compounds in organic solvents or liquid agrochemically active compounds (cf. WO 95-13 698) are already known. However, these preparations have the disadvantage that the release of the microencapsulated active compounds does not in all cases meet the requirements encountered in practice. Moreover, on storage, these formulations may cream, or they may form sediments.

This invention now provides novel microcapsule suspensions comprising

A) a particulate disperse phase of microcapsules, whose sleeves are reaction products of
mixtures of toluylene diisocyanate and 4,4'-methylenebis(cyclohexyl isocyanate) of the formula

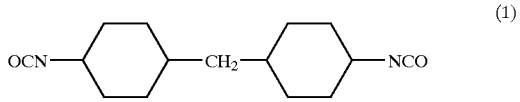

with
at least one diamine and/or polyamine,
and
which contain, as capsule filling
at least one solid agrochemically active compound from the group consisting of
the insecticidally active nicotinyls,
the insecticidally active pyrethroids,
the insecticidally active thiazole derivatives,
the insecticidally active phosphoric acid derivatives,
the fungicidally active azoles,
the herbicidally active triazolinones or benzonitriles and/or
the herbicidally active phenyluracils,
at least one liquid aliphatic hydrocarbon having a boiling point above 160° C.,
at least one oil-soluble polymeric dispersing agent and
optionally one or more agrochemically active compounds which are liquid at room temperature, and B) a liquid aqueous phase which, in addition to water, comprises
optionally additives and
optionally one or more agrochemically active compounds in non-encapsulated form which are solid at room temperature.

Furthermore, it has been found that microcapsule suspensions according to the invention are obtained when a) in a first step, a finely divided suspension of
at least one solid agrochemically active compound from the group consisting of
the insecticidally active nicotinyls,
the insecticidally active pyrethroids,
the insecticidally active thiazole derivatives,
the insecticidally active phosphoric acid derivatives,
the fungicidally active azoles,
the herbicidally active triazolinones or benzonitriles and/or the herbicidally active phenyluracils,
at least one liquid aliphatic hydrocarbon having a boiling point above 160° C.,
at least one oil-soluble polymeric dispersing agent and
a mixture of toluylene diisocyanate and 4,4'-methylenebis(cyclohexyl isocyanate) of the formula

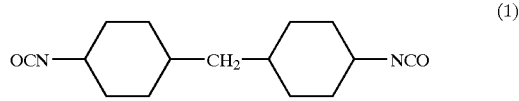

and also, if appropriate, one or more agrochemically active compounds which are liquid at room temperature,
is dispersed in an aqueous phase of
polyvinyl alcohol, if appropriate in a mixture with gum arabic, and
water, b) in a second step, at least one diamine and/or polyamine is added to the resulting mixture and c) in a third step,
additives and
optionally one or more further agrochemically active compounds in non-encapsulated form which are solid at room temperature
are added to the resulting microcapsule suspension.

Finally, it has been found that the microcapsule suspensions according to the invention are highly suitable for applying the agrochemically active compounds contained therein to plants and/or their habitat.

It is extremely surprising that the microcapsule suspensions according to the invention are more suitable for applying the agrochemically active compounds contained therein than the constitutionally most similar preparations of the prior art. It is particularly unexpected that, from among the numerous isocyanates suitable, it are specifically mixtures of toluylene diisocyanate and 4,4'-methylenebis (cyclohexyl isocyanate) of the formula (1) which are particularly suitable for preparing micro-capsule suspensions having the desired properties.

The microcapsule suspensions according to the invention have a number of advantages. Thus, they are capable of releasing the active components over a relatively long period of time in the amounts required in each case. Furthermore, it is favorable that the microcapsule suspensions according to the invention have high stability and, even on prolonged storage, neither cream nor form a sediment.

The microcapsule suspensions according to the invention are characterized by the components contained in the particulate disperse phase and in the aqueous phase.

The capsule sleeves of the microcapsules according to the invention are reaction products of the isocyanates and amines mentioned under (A).

Both toluylene diisocyanate and 4,4'-methylenebis (cyclohexyl isocyanate) are known.

Preferred amines of the groups listed under (A) are aliphatic and alicyclic primary and secondary diamines and polyamines. Examples which may be mentioned are ethylene-1,2-diamine, diethylenetriamine, triethylenetetramine, bis-(3-aminopropyl)-amine, bis-(2-methylaminoethyl)-methylamine, 1,4-di aminocyclohexane, 3-amino-1-methylaminopropane, N-methyl-bis-(3-aminopropyl)amine, 1,4-diamino-n-butane and 1,6-diamino-n-hexane.

Very particular preference is given to diethylenetriamine.

These diamines and polyamines are known compounds of organic chemistry.

The microcapsule suspensions according to the invention may comprise one or more solid agrochemically active compounds from the groups mentioned under (A).

Examples of insecticidally active nicotinyls which may be mentioned are imidacloprid, thiacloprid, thiamethoxam and acetamiprid.

Examples of insecticidally active pyrethroids which may be mentioned are betacyfluthrin, cypermethrin, transfluthrin and lambda-cyhalothrin.

An example of an insecticidally active thiazole derivative which may be mentioned is the active compound of the formula

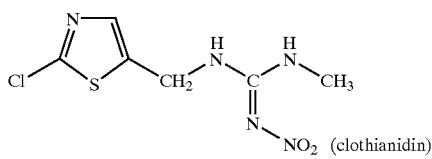

(2) (clothianidin)

An example of an insecticidally active phosphoric acid derivative which may be mentioned is azinphos-methyl.

Examples of fungicidally active azoles which may be mentioned are tebuconazole and 2-[2-(1-chlorocyclopropyl)-3-(2-chlorophenyl)-2-hydroxypropyl]-2,4-dihydro-[1,2,4]-triazole-3-thione.

Examples of herbicidally active triazolinones which may be mentioned are propoxycarbazone-sodium, flucarbazone-sodium and amicabazone.

An example of a herbicidally active benzonitrile which may be mentioned is dichlobenil.

Examples of herbicidally active phenyluracils which may be mentioned are the compounds of the formula

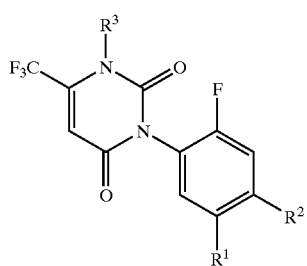

(II)

in which the substituents $R^1$, $R^2$ and $R^3$ are as defined below.

| $R^1$ | $R^2$ | $R^3$ |
|---|---|---|
| —N(SO$_2$—C$_2$H$_5$)(CO—C$_4$H$_9$-t) | —CN | —CH$_3$ |
| —N(SO$_2$—C$_2$H$_5$)(CO—CH$_3$) | —CN | —CH$_3$ |
| —N(SO$_2$—C$_2$H$_5$)(CO—C$_2$H$_5$) | —CN | —CH$_3$ |
| —N(SO$_2$—C$_2$H$_5$)(H) | —C(=S)—NH$_2$ | —CH$_3$ |
| —N(SO$_2$—C$_2$H$_5$)(CO—C$_3$H$_7$-i) | —CN | —CH$_3$ |
| —N(SO$_2$—C$_2$H$_5$)(CO—C$_4$H$_9$-n) | —CN | —CH$_3$ |
| —N(SO$_2$—C$_2$H$_5$)(CO—C$_3$H$_7$-n) | —CN | —CH$_3$ |
| —N(SO$_2$—CH$_3$)(CO—C$_4$H$_9$-t) | —CN | —CH$_3$ |
| —N(SO$_2$—CH$_3$)(CO—CH$_3$) | —CN | —CH$_3$ |
| —N(SO$_2$—CH$_3$)(CO—CH$_2$Cl) | —CN | —CH$_3$ |
| —N(SO$_2$—CH$_3$)(CO—C$_2$H$_5$) | —CN | —CH$_3$ |
| —N(SO$_2$—CH$_3$)(CO—C$_3$H$_7$-i) | —CN | —CH$_3$ |
| —N(SO$_2$—CH$_3$)(CO—C$_3$H$_7$-n) | —CN | —CH$_3$ |
| —N(SO$_2$—CH$_3$)(CO—CH=CH$_2$) | —CN | —CH$_3$ |
| —N(SO$_2$—CH$_3$)(CO—CH$_2$—OCH$_3$) | —CN | —CH$_3$ |
| —N(SO$_2$—C$_2$H$_5$)(CO—C$_4$H$_9$-t) | —CN | —NH$_2$ |

-continued

| R¹ | R² | R³ |
|---|---|---|
| ![N with SO₂—CH₃ and CO—C₄H₉-t] | —CN | —NH₂ |

Inside the capsules, the microcapsule suspensions according to the invention comprise at least one liquid aliphatic hydrocarbon having a boiling point above 160° C. Suitable hydrocarbons of this type are preferably paraffin oils and mineral oils. Examples which may be mentioned are the paraffin oils known under the names Norpare (from Exxon), Isopare (from Exxon) and Exxsol (from Exxon), and the mineral oil commercially available under the name BP Enerpar T 017 (from British Petrol).

Inside the capsules, the microcapsule suspensions according to the invention comprise at least one oil-soluble polymeric dispersant. Examples of dispersants of this type which may be mentioned are the products known under the names Atlox LP6 (from Uniqema), Agrimer AL 22 (from ISP Investments) and Hordaphos 215 (from Clariant).

Moreover, inside the capsules, the microcapsule suspensions according to the invention may also comprise one or more agrochemically active compounds which are liquid at room temperature.

The particles of the disperse phase have a mean particle size which is generally from 1 to 30 $\mu$m, preferably from 3 to 15 $\mu$m.

The aqueous phase of the microcapsule suspensions according to the invention consists essentially of water. Moreover, it may comprise additives, such as emulsifiers, dispersants, polyvinyl alcohol, mixtures of polyvinyl alcohol and gum arabic, antifoams, preservatives and thickeners.

In addition, the aqueous phase of the microcapsule suspensions according to the invention may also comprise one or more agrochemically active compounds in non-encapsulated form which are solid at room temperature.

Here, suitable emulsifiers and dispersants are preferably nonionic and anionic compounds having surface-active properties.

Examples of nonionic emulsifiers which may be mentioned are the products known under the names Pluronic PE 10 100 (from BASF) and Atlox 4913 (from Uniqema). Also suitable are tristyrylphenol ethoxylates. Examples of anionic emulsifiers which may be mentioned are the Bayer AG product Baykanol SL (=condensate of sulfonated ditolyl ether and formaldehyde), and also phosphated or sulfated tristyrylphenol ethoxylates, specifically Soprophor SLK and Soprophor 4D 384 (from Rhodia).

Polyvinyl alcohol or mixtures of polyvinyl alcohol with gum arabic may be present as protective colloids.

Suitable thickeners are all compounds which can easily be employed for this purpose in crop treatment agents. Preference is given to Kelzan® (thixotropic thickener based on xanthan), silicic acids and attapulgite.

Suitable preservatives are all substances which are usually present for this purpose in crop treatment agents. Examples which may be mentioned are Preventol® (Bayer AG) and Proxel®.

Suitable antifoams are compounds which can usually be employed for this purpose in crop treatment agents. Silane derivatives such as polydimethylsiloxane and magnesium stearate may be mentioned as being preferred.

Suitable agrochemically active compounds which may be present in the aqueous phase in non-encapsulated form are fungicides, insecticides and herbicides which are solid at room temperature.

Preferred fungicidally active compounds are carpropamid, fenhexamid, iprovalicarb, triadimefon, triadimenol, bitertanol, dichlobutrazole, tebuconazole, difenoconazole, cyproconazole, flutriafol, hexaconazol, myclobutanil, bromuconazole, epoxicona-zole, fenbuconazole, ipconazole, fluquinconazole, triticonazole, imibenconazole, imazalil, pencycuron, cresoxim-methyl, azoxystrobin, trifloxystrobin, probenazole, isoprothiolane, tricyclazole, dicyclocymet and phthalide.

Preferred insecticidally active compounds which may be mentioned are: azinphos-methyl, aminocarb, 2-sec-butylphenyl methylcarbamate, carbaryl, carbofuran, isoprocarb, methiocarb, mexacarbate, nabam, nitrilacarb, betacyfluthrin, imidacloprid and thiacloprid.

Preferred herbicidally active compounds which may be mentioned are: metazachlor, propachlor, flufenacet and metribuzin.

The aqueous phase comprises the agrochemically active compounds in non-encapsulated form, preferably in a ready-to-use formulation as a suspension.

The composition of the microcapsule suspensions according to the invention may be varied within a certain range. The proportion of the disperse encapsulated phase, based on the entire formulation, is generally from 5 to 70% by weight, preferably from 45 to 50% by weight. Within the disperse encapsulated phase, too, the proportion of the individual components may be varied within a certain range. Thus, in the disperse phase, the concentrations of reaction product of mixtures of toluylene diiusocyanate and 4,4'-methylene-bis(cyclohexyl isocyanate) with diamine and/or polyamine are generally from 1 to 12% by weight, preferably from 2 to 10% by weight, of solid agrochemically active compounds are generally from 10 to 90% by weight, preferably from 10 to 80% by weight, of aliphatic hydrocarbon are generally from 10 to 90% by weight, preferably from 30 to 70% by weight, of oil-soluble polymeric dispersant are generally from 1 to 15% by weight, preferably from 3 to 10% by weight, and of agrochemically active compounds which are liquid at room temperature are generally from 0 to 20% by weight, preferably from 0 to 10% by weight.

In the aqueous phase, the proportion of additives can be varied within a relatively wide range. Based on the total aqueous phase, the concentration of additives is generally from 3 to 25% by weight, preferably from 5 to 20% by weight.

The proportion of agrochemical non-encapsulated active compounds in the aqueous phase can also be varied within a relatively wide range. Thus, based on the total aqueous phase, the concentration of agrochemically active compounds is generally between 0 and 40% by weight, preferably between 0 and 30% by weight.

Preferred microcapsule suspensions according to the invention which comprise in each case one agrochemically active compound both in the disperse phase inside the microcapsules and in the aqueous phase which may be mentioned are the following formulations:

Suspension with imidacloprid in microencapsulated form and carpropamid in the aqueous phase in the form of a suspension.

Suspension with imidacloprid in microencapsulated form and azinphos-methyl in the aqueous phase in the form of a suspension.

Suspension with betacyfluthrin in microencapsulated form and betacyfluthrin in the aqueous phase.

The microcapsule suspensions according to the invention are prepared by microencapsulation.

In general, this is achieved by initially preparing a finely divided suspension of at least one optionally pre-ground solid agrochemically active compound from the groups mentioned, at least one liquid aliphatic hydrocarbon having a boiling point above 160° C., at least one oil-soluble polymeric dispersant and a mixture of toluylene diisocyanate and 4,4'-methylenebis (cyclohexyl isocyanate) and also if appropriate one or more agrochemically active compounds which are liquid at room temperature by mixing the components.

Here, the amounts of the individual components are chosen such that they are present in the resulting disperse phase in the concentrations already mentioned. The ratio of toluylene diisocyanate to 4,4'-methylenebis(cyclohexyl isocyanate) of the formula (1) may be varied within a certain range. Per part by weight of toluylene diisocyanate, in general from 0.3 to 2 parts by weight, preferably from 0.5 to 1.5 parts by weight, of 4,4'-methylenebis(cyclohexyl isocyanate) are used.

During the preparation of the suspension (=organic phase), the temperatures may be varied within a certain range. In general, the preparation is carried out at temperatures of from 10 to 60° C., preferably from 20 to 50° C.

Furthermore, an aqueous phase is prepared by stirring polyvinyl alcohol, optionally in a mixture with gum arabic, into water.

Here, the amounts of the individual components are again chosen such that they are present in the resulting disperse phase in the concentrations already mentioned. The ratio of polyvinyl alcohol to gum arabic can be varied within a certain range. Per part by weight of polyvinyl alcohol, in general from 0 to 10 parts by weight, preferably from 0 to 5 parts by weight, of gum arabic are used.

During the preparation of the aqueous phase, too, the temperatures may be varied within a certain range. In general, the preparation is carried out at temperatures from 20° C. to 100° C., preferably from 30° C. to 90° C.

With vigorous stirring or mixing, the organic phase is then dispersed in the aqueous phase.

For preparing the dispersions, it is possible to use all apparatus generating strong sheer forces and customarily used for such purposes. Rotor/stator mixers and jet dispersers may be mentioned by way of example.

During the preparation of the dispersions, too, the temperatures may be varied within a certain range. In general, the preparation is carried out at temperatures from 10° C. to 40° C., preferably from 10° C. to 30° C.

In the second step of the process according to the invention, the dispersion prepared in the first step is, with slow stirring, admixed with at least one diamine and/or polyamine, and stirring is then continued until the microencapsulation reaction that sets in has finished.

Here, preferred reaction components are all those diamines and polyamines which have already been mentioned in connection with the description of the microcapsule suspensions according to the invention as being preferred.

When carrying out this second step of the process according to the invention, the ratio of isocyanate to amine component can be varied within a certain range. In general, from 0.8 to 1.5 equivalents of amine component are employed per mole of isocyanate. The amounts of isocyanate and amine are preferably chosen such that equimolar amounts of isocyanate and amino groups are present.

When carrying out the second step of the process according to the invention, the reaction temperatures can be varied within a certain range. In general, the reaction is carried out at temperatures from 40 C. to 80° C., preferably from 50° C. to 70° C.

In the third step of the process according to the invention, additives and optionally further solid agrochemically active compounds in non-encapsulated form, the latter preferably in the form of suspension concentrates, are added, if appropriate with stirring, to the microcapsule suspension prepared beforehand.

Here, suitable additives are thickeners, preservatives, antifoams and dispersants. Preference is given to using those substances which have already been mentioned in connection with the description of the microcapsule suspensions according to the invention as being preferred thickeners, preservatives, antifoams and dispersants. Suitable agrochemically active compounds are those which have already been mentioned in connection with the description of the microcapsule suspensions according to the invention as agrochemical components of the aqueous phase.

When carrying out the third step of the process according to the invention, the temperatures can again be varied within a certain range. In general, the process step is carried out at temperatures from 10° C. to 50° C., preferably from 10° C. to 40° C.

The process according to the invention is generally carried out under atmospheric pressure.

In the manner described above, it is possible to prepare the microcapsule suspensions according to the invention in amounts of about 500 ml without any problems., If it is desired to prepare larger amounts, the process according to the invention is advantageously carried out continuously. This is generally effected by adding the amounts of organic phase and aqueous phase desired in each case accurately from separate storage vessels with the aid of two pumps, followed by dispersion in a dispersing apparatus using a rotor/stator mixer, and this dispersion is then continuously transferred into a further vessel and allowed to react with added amine, and the resulting microcapsule suspension is, if appropriate, then admixed with additives and optionally also solid agrochemically active compounds, preferably in the form of commercial suspension concentrates.

The microcapsule suspensions according to the invention are highly suitable for applying the agrochemically active compounds contained therein to plants and/or their habitat. They ensure that the active components are released in the amounts desired in each case, over a relatively long period of time.

In practice, the microcapsule suspensions according to the invention can be used either as such or after prior dilution with water. Application is carried out by customary methods, i.e., for example, by watering, spraying or atomizing. However, it is also possible to remove the aqueous phase and to apply the free-flowing solid product that remains by customary methods.

The application rate of the microcapsule suspensions according to the invention can be varied within a relatively wide range. It depends on the agrochemically active compounds in question and their content in the microcapsule suspensions.

The invention is illustrated by the examples below.

PREPARATION EXAMPLES

Example 1 a) Organic Phase

At room temperature, 320 g of a finely ground suspension of 1534.4 g of imidacloprid, 300 g of Atiox LP6 and 1175.6 g of mineral oil (PB Enerpar T 017) are, with stirring, mixed with 16.4 g of toluylene diisocyanate and 12.4 g of 4,4'-methylenebis(cyclohexyl isocyanate).

b) Aqueous Phase

With heating to 70° C. and stirring, 12.0 g of polyvinyl alcohol (Moviol 4-88) and 4 g of gum arabic are dissolved in 333.6 g of deionized water. The solution is then cooled in an ice bath.

c) Microcapsule Suspension

At room temperature, organic phase and aqueous phase are, in a ratio of 48:52, in an amount of altogether 202 ml/min, conveyed and emulsified in a rotor/stator mixer at 20 000 rotations per minute. At temperatures below 20° C., 20 g of a 50 percent by weight strength solution of diethylenetriamine are added to the resulting suspension which is then, with stirring, heated to 55° C. over a period of one hour and then stirred at 55° C. for 20 hours. After cooling to room temperature, 0.8 g of Preventol D2, 0.8 g of Preventol D7, 30 g of Baykanol SL and 44 g of a 2% by weight strength solution of Kelzan S (thickener based on xanthan) in water are added.

This gives 800 g of a microcapsule suspension having an imidacloprid content of 20% by weight and a mean particle size of 11.4 μm.

Example 2 a) Organic Phase

At room temperature, 1000 g of a finely ground suspension of 1016.26 g of imidacloprid, 200 g of Atlox LP6 and 783.74 g of mineral oil (BP Enerpar T 017) are, with stirring, mixed with 47.07 g of toluylene diisocyanate and 35.43 g of 4,4'-methylenebis(cyclohexyl isocyanate).

b) Aqueous Phase

With heating to 70° C. and stirring, 12.5 g of polyvinyl alcohol (Moviol 4-88) and 62.5 g of gum arabic are dissolved in 1282.5 g of deionized water. The solution is then cooled to room temperature.

c) Microcapsule Suspension

At room temperature, the organic phase and the aqueous phase are, in a ratio of 48:52, conveyed with the aid of pumps into a reaction vessel and emulsified using a rotor/stator mixer at 20 000 rotations per minute. At a temperature of about 15° C., a mixture of 27.5 g of diethylenetriamine and 27.5 g of water is added to the resulting emulsion, which is then heated with stirring to 50° C. over a period of one hour and then stirred at 50° C. for 20 hours. After cooling to room temperature, 2.5 g of Preventol D2, 2.5 g of Preventol D7, 56.25 g of Soprophor 4D 384, 56.25 g of Pluronic PE 10 100 and 75 g of a 2% strength by weight solution of Kelzan S (thickener based on xanthan) in water are added.

This gives a microcapsule suspension having an imidacloprid content of 18.44% by weight and a mean particle size of 11.8 μm.

Example 3

829.2 g of the microcapsule suspension according to Example 2 are, at room temperature and with stirring, mixed with 712.4 g of a commercial suspension concentrate comprising 40% by weight of carpropamid, 7% by weight of emulsifiers and dispersants, 10% by weight of antifreeze, preservative and thickeners and 43% by weight of water and with 57.4 g of deionized water. This gives a combination formulation of encapsulated imidachloprid (100 g/l) and non-encapsulated carpropamid (191 g/l)

having a density of 1.085 g/ml.

USE EXAMPLES

Example A

Release of Active Compound

In each case, a defined amount of a formulation comprising imidacloprid as active compound is suspended in 500 ml of water and then left at room temperature. After 48 hours, in each case 5 ml are withdrawn and, to remove the solid components, filtered. Using HPLC, the content of imidacloprid in the aqueous phase is then determined.

The test results are shown in the table below.

TABLE A

| Release of active compound | | |
|---|---|---|
| Formulation according to Example No. | Amount of formulation weighed out | Content of imidacloprid in the aqueous phase |
| according to the invention | | |
| 1 | 2.7 g | 5.3 ppm |
| 2 | 2.5 g | 6.0 ppm |
| 3 | 4.4 g | 10.5 ppm |
| Known | | |
| commercial suspension | 0.5 g | 501 ppm* |

*The imidacloprid content was measured after the dilute formulation had stood for just two hours.

Example B

Comparibility Test

In each case 12 g of rice grains of the variety Kusabue are evenly sown in dishes of the dimensions 10 cm×10 cm whose bottom is covered with soil up to a height of 4 cm. Before the rice grains are then covered with a layer of soil of a height of 1 cm, per dish in each case 28 ml of formulation comprising the amount of active compound given in each case are applied evenly over the entire area by watering.

The dishes are then placed in a chamber in which the daytime temperature is 24° C. and the night-time temperature is 15° C.

28 days after sowing, the plants are examined for damage. What is determined are in each case necroses, yellowing, disturbed growth and deformations. The sum of all damage is expressed in percent. 0% means that no damage occurs, whereas 100% means that the plants are completely affected by the damage in question.

The preparations used, the application rates of active compound and the test results are shown in the tables below.

TABLE B-1

Compatibility test

| Formulation according to Example | Application rate of active compound | Sum of damage in % |
|---|---|---|
| Known | | |
| A | 24 mg | 20 |
|  | 48 mg | 30 |
|  | 120 mg | 60 |
| according to the invention | | |
| 1 | 24 mg | 15 |
|  | 48 mg | 13 |
|  | 120 mg | 18 |

A = Commercial formulation of imidacloprid (non-encapsulated)

TABLE B-2

Compatibility test

| Formulation according to Example | Application rate of active compound imidacloprid/carpropamid | Sum of damage in % |
|---|---|---|
| Known | | |
| B | 24 mg/40 mg | 10 |
|  | 48 mg/80 mg | 15 |
|  | 120 mg/200 mg | 35 |
| according to the invention | | |
| 3 | 24 mg/40 mg | 5 |
|  | 48 mg/80 mg | 5 |
|  | 120 mg/200 mg | 10 |

B = Commercial formulation of imidacloprid and carpropamid (neither of them encapsulated)

What is claimed is:

1. A microcapsule suspension comprising:
   (A) a particulate disperse phase of microcapsules comprising
       (1) sleeves that are reaction products of mixtures of toluylene diisocyanate and 4,4'-methylenebis(cyclohexyl isocyanate) of the formula:

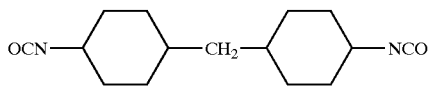

(1)

with at least one diamine and/or polyamine, and
       (2) a capsule filling comprising:
           (i) at least one solid agrochemically active compound selected from the group consisting of insecticidally active nicotinyls, insecticidally active pyrethroids, insecticidally active thiazole derivatives, insecticidally active phosphoric acid derivatives, fungicidally active azoles, herbicidally active triazolinones or benzonitriles, and herbicidally active phenyluracils,
           (ii) at least one liquid aliphatic hydrocarbon having a boiling point above 160° C.,
           (iii) at least one oil-soluble polymeric dispersing agent, and
           (iv) optionally, one or more agrochemically active compounds that are liquid at room temperature, and
   (B) a liquid aqueous phase comprising:
       (1) water,
       (2) optionally, additives, and
       (3) optionally, one or more agrochemically active compounds in non-encapsulated form that are solid at room temperature.

2. A process for preparing a microcapsule suspension according to claim 1 comprising:
   (a) in a first step, dispersing a finely divided suspension of:
       (i) at least one solid agrochemically active compound selected from the group consisting of insecticidally active nicotinyls, insecticidally active pyrethroids, insecticidally active thiazole derivatives, insecticidally active phosphoric acid derivatives, fungicidally active azoles, herbicidally active triazolinones or benzonitriles, and herbicidally active phenyluracils,
       (ii) at least one liquid aliphatic hydrocarbon having a boiling point above 160° C.,
       (iii) at least one oil-soluble polymeric dispersing agent,
       (iv) a mixture of toluylene diisocyanate and 4,4'-methylenebis(cyclohexyl isocyanate) of the formula:

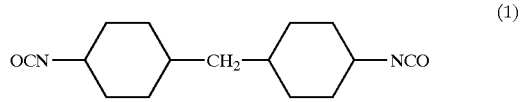

(1)

(v) optionally, one or more agrochemically active compounds that are liquid at room temperature, in an aqueous phase of polyvinyl alcohol, optionally in a mixture with gum arabic, and water,
   (b) in a second step, adding to the resulting mixture from step (a) at least one diamine and/or polyamine, and
   (c) in a third step, adding to the resulting microcapsule suspension from step (b)
       (i) additives, and
       (ii) optionally, one or more further agrochemically active compounds in non-encapsulated form that are solid at room temperature.

3. A method for applying the agrochemically active compounds to plants and/or, their habitat comprising applying a microcapsule suspension according to claim 1 to plants and/or their habitat.

4. A microcapsule suspension according to claim 1 comprising imidacloprid in microencapsulated form.

5. A microcapsule suspension according to claim 1 comprising carpropamid in non-encapsulated form in the liquid aqueous phase.

6. A microcapsule suspension according to claim 1 comprising imidacloprid in microencapsulated form and carpropamid in non-encapsulated form.

* * * * *